US012213543B2

(12) United States Patent
Walker (10) Patent No.: US 12,213,543 B2
(45) Date of Patent: *Feb. 4, 2025

(54) SENSE-ENABLED APPAREL (71) Applicant: NIKE, Inc., Beaverton, OR (US)

(72) Inventor: Steven H. Walker, Camas, WA (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/241,601

(22) Filed: Sep. 1, 2023

(65) Prior Publication Data

US 2023/0404185 A1 Dec. 21, 2023

Related U.S. Application Data

(60) Continuation of application No. 17/576,756, filed on Jan. 14, 2022, now Pat. No. 11,771,151, which is a
(Continued)

(51) Int. Cl.
*A41D 3/00* (2006.01)
*A41B 1/08* (2006.01)
(Continued)

(52) U.S. Cl.
CPC ............... *A41D 13/01* (2013.01); *A41B 1/08* (2013.01); *A41D 1/005* (2013.01); *A41D 1/04* (2013.01);
(Continued)

(58) Field of Classification Search
CPC .......... A41D 1/00; A41D 1/002; A41D 1/005; A41D 1/02; A41D 1/04; A41D 1/06;
(Continued)

(56) References Cited

U.S. PATENT DOCUMENTS 2,494,917 A   1/1950 Van Liempt
5,457,900 A   10/1995 Roy et al.
(Continued)

FOREIGN PATENT DOCUMENTS

CN   101611934 A   12/2009
CN   205411164 U   8/2016
(Continued)

OTHER PUBLICATIONS

Dec. 10, 2018—(WO) ISR & WO—App. No. PCT/US18/049036.
May 19, 2022—(EP) ESR—EP 22159601.8.

*Primary Examiner* — Jason M Crawford (74) *Attorney, Agent, or Firm* — Banner & Witcoff, Ltd.

(57) ABSTRACT

Systems and methods for integrating and using sensor system in articles of apparel are provided. The system may include an apparel piece sized and dimensioned to be worn on a user and a sensor system integrated with the apparel piece. The sensor system may include at least one stretchable capacitive sensor positioned on the apparel piece so as to measure a biometric parameter of the user when the apparel piece is worn, an illumination system configured to provide illumination in a specified illumination area based on the measured biometric parameter of the user, and a control module to control one or more settings of the illumination system.

20 Claims, 7 Drawing Sheets

Related U.S. Application Data continuation of application No. 16/890,109, filed on Jun. 2, 2020, now Pat. No. 11,253,012, which is a division of application No. 16/117,566, filed on Aug. 30, 2018, now Pat. No. 10,701,987.

(60) Provisional application No. 62/552,756, filed on Aug. 31, 2017.

(51) Int. Cl.
| | |
|---|---|
| A41D 1/00 | (2018.01) |
| A41D 1/04 | (2006.01) |
| A41D 1/06 | (2006.01) |
| A41D 1/089 | (2018.01) |
| A41D 13/01 | (2006.01) |
| A41D 27/08 | (2006.01) |
| A61B 5/00 | (2006.01) |
| A61B 5/11 | (2006.01) |
| F21V 23/00 | (2015.01) |
| F21V 23/04 | (2006.01) |
| F21V 33/00 | (2006.01) |
| G01L 1/14 | (2006.01) |
| A63B 71/06 | (2006.01) |
| F21Y 115/10 | (2016.01) |

(52) U.S. Cl.
CPC ............... *A41D 1/06* (2013.01); *A41D 1/089* (2018.01); *A41D 3/00* (2013.01); *A41D 27/085* (2013.01); *A61B 5/112* (2013.01); *A61B 5/6805* (2013.01); *F21V 23/008* (2013.01); *F21V 23/0471* (2013.01); *F21V 33/0008* (2013.01); *G01L 1/142* (2013.01); *A61B 5/742* (2013.01); *A61B 5/7475* (2013.01); *A61B 2562/0261* (2013.01); *A63B 71/0622* (2013.01); *A63B 2220/58* (2013.01); *A63B 2220/836* (2013.01); *A63B 2225/50* (2013.01); *F21Y 2115/10* (2016.08)

(58) Field of Classification Search
CPC .. A41D 1/08; A41D 3/00; A41F 27/08; A41F 27/085; F21V 33/00; F21V 33/0004; F21V 33/0008; F21V 23/0471; A63B 2220/836; A61B 5/112
See application file for complete search history.

(56) References Cited

U.S. PATENT DOCUMENTS

| | | | | |
|---|---|---|---|---|
| 5,690,411 | A * | 11/1997 | Jackman | G08B 5/006 |
| | | | | 362/108 |
| 10,065,074 | B1 * | 9/2018 | Hoang | G01P 1/02 |
| 10,701,987 | B2 * | 7/2020 | Walker | A41D 27/085 |
| 11,253,012 | B2 * | 2/2022 | Walker | A41D 13/01 |
| 11,771,151 | B2 * | 10/2023 | Walker | A41D 3/00 |
| | | | | 315/307 |
| 2010/0251453 | A1 * | 10/2010 | Chen | G08B 5/004 |
| | | | | 340/815.45 |
| 2011/0087115 | A1 * | 4/2011 | Sackner | A61B 5/0535 |
| | | | | 600/484 |
| 2012/0246795 | A1 * | 10/2012 | Scheffler | A61B 5/0205 |
| | | | | 2/243.1 |
| 2013/0274904 | A1 * | 10/2013 | Coza | A61B 5/162 |
| | | | | 700/91 |
| 2014/0070957 | A1 * | 3/2014 | Longinotti-Buitoni | |
| | | | | A61B 5/02055 |
| | | | | 340/870.01 |
| 2014/0318699 | A1 * | 10/2014 | Longinotti-Buitoni | |
| | | | | H05K 1/095 |
| | | | | 156/247 |
| 2015/0145671 | A1 * | 5/2015 | Cohen | G06Q 30/0241 |
| | | | | 340/539.11 |
| 2015/0250420 | A1 * | 9/2015 | Longinotti-Buitoni | |
| | | | | A61B 5/1135 |
| | | | | 600/534 |
| 2015/0309563 | A1 * | 10/2015 | Connor | A61B 5/1071 |
| | | | | 73/865.4 |
| 2015/0370320 | A1 * | 12/2015 | Connor | A61B 5/1121 |
| | | | | 345/173 |
| 2016/0038083 | A1 * | 2/2016 | Ding | A61B 5/1135 |
| | | | | 600/388 |
| 2016/0284436 | A1 * | 9/2016 | Fukuhara | H01B 1/026 |
| 2016/0338644 | A1 * | 11/2016 | Connor | A61B 5/1126 |
| 2017/0196513 | A1 * | 7/2017 | Longinotti-Buitoni | |
| | | | | D06P 1/5285 |
| 2017/0274249 | A1 * | 9/2017 | Moebius | A63B 23/0405 |
| 2017/0325518 | A1 * | 11/2017 | Poupyrev | D03D 1/0088 |
| 2017/0360122 | A1 * | 12/2017 | Chin | F41H 5/0492 |
| 2017/0363279 | A1 * | 12/2017 | Macias | F21L 4/00 |
| 2018/0027909 | A1 * | 2/2018 | Bangera | A41D 13/018 |
| 2018/0093121 | A1 * | 4/2018 | Matsuura | G09B 19/0038 |
| 2018/0242654 | A1 * | 8/2018 | Marikkar | A61B 5/7455 |
| 2018/0310659 | A1 * | 11/2018 | Poupyrev | A63B 43/004 |
| 2019/0059461 | A1 * | 2/2019 | Walker | A41D 1/005 |
| 2020/0068708 | A1 * | 2/2020 | Longinotti-Buitoni | |
| | | | | A41D 13/1281 |
| 2020/0297045 | A1 * | 9/2020 | Walker | A61B 5/6805 |
| 2021/0069525 | A1 * | 3/2021 | Schupp | A41D 1/002 |
| 2021/0298672 | A1 * | 9/2021 | Lee | A61B 5/7445 |
| 2022/0132946 | A1 * | 5/2022 | Walker | F21V 33/0008 |
| | | | | 315/307 |
| 2022/0408854 | A1 * | 12/2022 | Alipour | G01L 1/205 |
| 2023/0404185 | A1 * | 12/2023 | Walker | G01L 1/142 |
| 2024/0074709 | A1 * | 3/2024 | Capodilupo | A61B 5/02438 |

FOREIGN PATENT DOCUMENTS

| | | |
|---|---|---|
| GB | 2494917 A | 3/2013 |
| JP | H09250009 A | 9/1997 |
| JP | 2001089908 A | 4/2001 |
| JP | 2005146499 A | 6/2005 |
| JP | 2012214968 A | 11/2012 |
| JP | 2015017335 A | 1/2015 |
| JP | 2016072846 A | 5/2016 |
| JP | 2017141538 A | 8/2017 |
| JP | 2017522062 A | 8/2017 |
| KR | 20110131661 A | 12/2011 |
| KR | 20150125535 A | 11/2015 |
| WO | 2014204323 A1 | 12/2014 |
| WO | 2017096044 A1 | 6/2017 |

* cited by examiner

SENSE-ENABLED APPAREL

CROSS-REFERENCE TO RELATED APPLICATION

This application is a continuation of U.S. patent application Ser. No. 17/576,756, filed Jan. 14, 2022, which is a continuation of U.S. patent application Ser. No. 16/890,109, filed Jun. 2, 2020, now U.S. Pat. No. 11,253,012, which is a divisional of U.S. patent application Ser. No. 16/117,566, filed on Aug. 30, 2018, and now granted as U.S. Pat. No. 10,701,987, which claims priority to U.S. Provisional Application Ser. No. 62/552,756, and filed on Aug. 31, 2017. The contents of these applications are hereby incorporated by reference in their entireties for all purposes.

BACKGROUND

Articles of apparel or footwear having sensor systems incorporated therein are known. Sensor systems may track movement and sense, measure, and/or collect performance data. Such systems may provide an enhanced workout experience based on sensed information. Known sensor-integrated apparel designs often have significant impacts on the weight, softness, and/or flexibility of the apparel, and/or often require some amount of disassembly in order to wash the apparel.

Therefore, improved systems and methods to address these and other shortcomings in the art are desired.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of this disclosure relate to sensor-integrated apparel systems configured to sense biometric information of a wearer. Example embodiments may relate to a system, method, apparatus that include sensor-integrated garments and/or uses thereof. Certain implementations may include a garment sized and dimensioned to be worn by a user and a sensor system integrated into the garment. The sensor system includes at least one stretchable capacitive fabric sensor, a control module and an illumination system. The at least one stretchable capacitive sensor is integrated onto the garment so as to measure at least one biometric parameter of the user when the garment is worn. The illumination system includes at least one light emitting diode (LED) module and is configured to provide illumination to a designated area. The control module is configured to control and operably connect to the capacitive sensor and the illumination system.

In some embodiments, the garment may be a shirt or jacket and the at least one capacitive sensor may include a pair of sensors. Each sensor may be positioned to correspond to right and left deltoids of the user and be configured to sense an arm swing of the user. Each deltoid sensor may be configured to sense a strain indicative of an arm swing of the user. In some embodiments, the garment may be a pair of pants or shorts, and the at least one capacitive sensor may be positioned to correspond to the right and left ankles, knees, thighs, etc. of the user and be configured to sense a pace or leg swing of the user.

The illumination system may be configured to adjust an intensity and/or a duration of illumination based on one or more settings from the control module. The control module may also be operably connected to additional sensors, e.g., including a time/intensity sensor configured to receive a user input specifying a setting of the illumination system, and/or a mode sensor configured to receive a user input specifying a mode of operation of the illumination system and to power on/off the illumination system. The time/intensity sensor and the mode sensor may be positioned in particular locations on the garment so as to provide ease of access to a user to provide inputs thereon. The control module may be positioned on a particular location on the garment so as not to obstruct the user when the garment is worn and/or when performing an activity. The mode sensor may include input selectors corresponding to a continuous mode and a pace mode. The time/intensity sensor may include input selectors configured to adjust an intensity of the illumination system, and to adjust a frequency of a pulsation of the illumination system.

The control module may be configured to be disconnectable from the sensor system and removable from the garment. The control module may include a hermetically sealed outer shell encasing electronic and other components therein. The hermetically sealed outer shell may be shaped so as to contour a portion of the user in accordance with a location of the control module when affixed to the garment. The control module may include a battery and a printed circuit board assembly. The control module may be configured to allow recharging of the battery without disassembly or removal of the battery therefrom. The control module may be configured to be removable from the garment and connectable to a computing device for transfer of data therebetween.

The illumination system may be configured to have a targeted and/or controllable illumination area based on a selected mode of operation. The illumination system may include a controllable directional component configured to adjust the illumination area. The illumination system may include an inboard LED module and an outboard LED module. A twisted wire armature or spine may connect to inboard and outboard LED modules. A flexible printed circuit board may electrically connect the inboard and outboard LED module and connect the illumination system to the sensor system and/or the control module. The illumination system be include a casing housing various components therein. For example, a clear rubber casing that forms a watertight seal may be provided. Portions of the LED modules in the illumination system may be bendable or movable to adjust the illumination area.

The sensor system, the illumination system, and the control module may be interconnected in the garment by wiring routed along seams of the garment. In some embodiments, the wiring may be comprised of a flexible, thin metallized thread. In some embodiments, the wiring may be comprised of a tape including thermal plastic urethane film with conductive ink traces that is radio frequency (RF) or thermally bonded to the garment.

In some embodiments, a method for providing illumination from a garment as a user performs an athletic activity is provided. The method may include sensing a strain from one or more sensors located on the garment, determining a pace or a predicted next movement of the user based on the sensed strain, and causing an illumination system on the garment to illuminate a portion of the user's path based on the determined pace or predicted next movement. The method may further include determining a side of a next footstrike based on the determined pace. Causing the illumination system to illuminate may then include illuminating an area of the user's path corresponding to the determined side of the next footstrike. The method may further include adjusting a duration of illumination of the user's path in response to a user-provided input. The method may further include adjusting the illumination system to provide a constant illumination in response to a user-provided input.

These and other aspects of the embodiments are discussed in greater detail throughout this disclosure, including the accompanying drawings.

BRIEF DESCRIPTION OF THE DRAWINGS

The present disclosure is illustrated by way of example and not limited in the accompanying figures in which like reference numerals indicate similar elements.

FIGS. 1A-B illustrate an exemplary sensor-integrated apparel system in accordance with example embodiments, wherein FIG. 1A illustrates a front view, and FIG. 1B illustrates a rear view.

FIGS. 6A-B illustrate another exemplary sensor-integrated apparel system in accordance with example embodiments, wherein FIG. 6A illustrates a front view, and FIG. 6B illustrates a rear view.

DETAILED DESCRIPTION

In the following description of the various embodiments, reference is made to the accompanying drawings, which form a part hereof, and in which is shown by way of illustration various embodiments in which the disclosure may be practiced. It is to be understood that other embodiments may be utilized and structural and functional modifications may be made without departing from the scope and spirit of the present disclosure. Further, headings within this disclosure should not be considered as limiting aspects of the disclosure. Those skilled in the art with the benefit of this disclosure will appreciate that the example embodiments are not limited to the example headings.

Figure 1A:
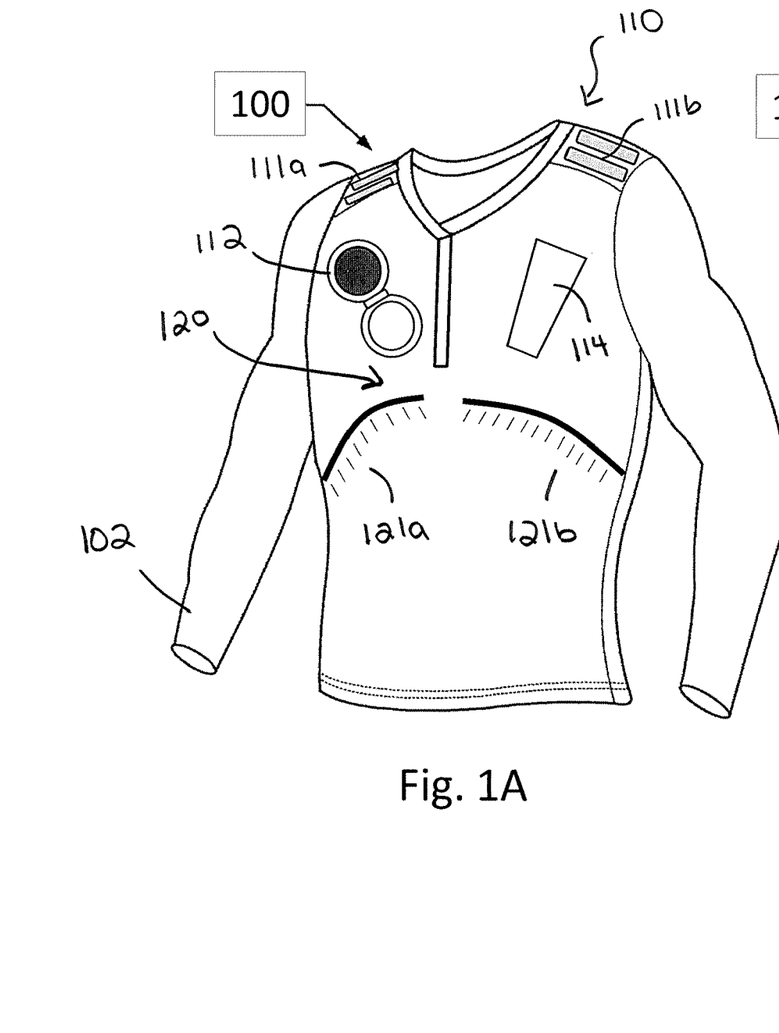
Figure 1B:
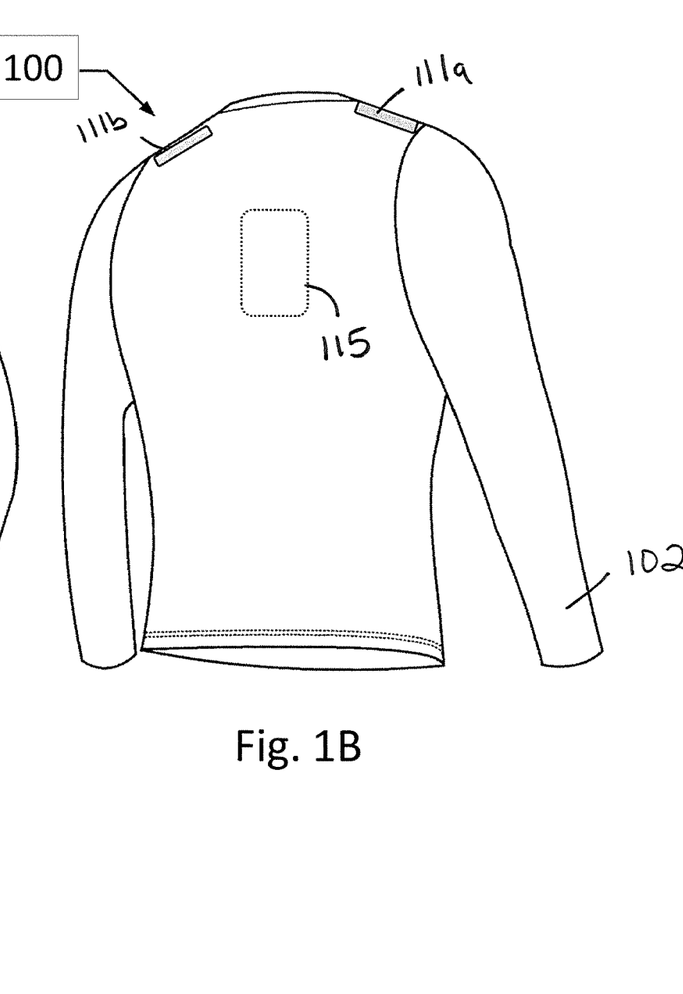

FIGS. 1A and 1B illustrates an example of a sensor integrated apparel system 100 in accordance with example embodiments. Example system 100 may include one or more apparel pieces, such as garment 102, sized and designed to be worn on a user. Garment 102 may include a shirt, such as a long sleeve, short sleeve, tank top or vest. In other embodiments, garment 102 may include a pair of pants, socks, footwear, body suit, outerwear, and/or any other desired type of apparel. In certain configurations, garment 102 may be comprised of cotton, nylon, polyester, spandex or other types of fabric typically used for apparel and/or worn during an athletic activity. Different classes of apparel may be utilized in which a given class of apparel has specific sensors configured to be located proximate to a specific portion of the user's body when properly worn. For example, golf apparel may include one or more sensors positioned on the apparel in a first configuration and yet soccer apparel may include one or more sensors positioned on apparel in a second configuration. Those skilled in the art will appreciate that other configurations are possible.

System 100 may be configured with a sensor system 110 integrated with garment 102 and configured to sense biometric information of a wearer, among other things. Sensor system 110 may include one or more sensors configured to sense, detect, and/or measure athletic movement from a user. The sensor system 110 may include at least one stretchable capacitive sensor (e.g., sensors 111a and 111b), a control module 115 and an illumination system 120. In certain embodiments, sensor system 110 may be integrated into garment 102, which may be any type of apparel, such as athletic clothing. Sensor system 110 may be incorporated into garment 102 and/or placed at any desired location of garment 102 corresponding to a part of the body of a wearer. Parts of the sensor system 110 may communicate (e.g., via flexible wiring in the article of clothing or wirelessly) with each other, including communication with the at least one stretchable capacitive fabric sensor, control module 115 and/or illumination system 120. Examples of garment systems are described immediately below, however, these are merely example embodiments and this disclosure should not be limited to such.

The illumination system 120 of FIGS. 1A and 1B includes a pair of LED modules 121a and 121b on respective sides of a front of garment 102, and the LED modules 121a and 121b may be configured to provide illumination to a designated area. The control module 115 may be configured to control and operably connect to the capacitive sensor and the illumination system 120. Additional components of sensor system 110 may be provided in addition to those illustrated in FIGS. 1A and 1B. Indeed, sensor system 110 may include more than one instance of each component (e.g., more than one capacitive fabric sensor, more than one illumination system 120, etc.).

In certain embodiments, sensor system 110 may comprise a sensor assembly that includes a plurality of different sensors, e.g., in addition to at least one stretchable capacitive sensor. In an example embodiment, the sensor assembly may include, or permit operative connection to, an accelerometer (including in the form of a multi-axis accelerometer), a gyroscope, a location-determining device (e.g., GPS), a light sensor, a temperature sensor (including ambient temperature and/or body temperature), a heart rate monitor, an image-capturing sensor, a moisture sensor and/or combinations thereof. Detected movements or parameters from device's sensor(s), may include (or be used to form) a variety of different parameters, metrics or physiological characteristics including but not limited to speed, distance, steps taken, and energy expenditure such as calories, heart rate and sweat detection. Such parameters may also be expressed in terms of activity points or currency earned by the user based on the activity of the user.

Sensor system 110 may be utilized in detecting and/or measuring athletic movements of a user wearing garment 102. In one embodiment, data obtained by sensor system 110 may directly detect athletic movements, such that the data obtained from sensor system 110 is directly correlated to a motion parameter. Sensor system 110 may include at least one stretchable capacitive fabric sensor. The at least one stretchable capacitive fabric sensor may be integrated into construction of garment 102, and the fabric sensor may sense tensile, compression, and/or sliding modes. Various fabric sensors of system 100 may be grouped in particular locations and/or be located symmetrically about garment 102. For example, six fabric sensors are provided in system 100 of FIGS. 1A and 1B—a pair of a right side strain sensors 111a and a pair of left side strain sensors 111b, a mode sensor 112, and a time/intensity sensor 114. One skilled in the art would understand that various other combinations and number of sensors may be employed in sensor system 110. Example uses of illustrative sensor system 110 are provided herein.

Mode sensor 112 and time/intensity sensor 114 may each include one or more input mechanisms, such as a button, to assist in operation of the system 100. The button may be a depressible or touch screen input operably connected to control module 115 and/or any other electronic components, such as one or more elements of the type(s) discussed in relation to sensor system 110. Control module 115 may be embedded or otherwise part of garment 102. Garment 102 may be formed of one or more materials, including textile components and may include one or more displays (not pictured). A display may be considered an illuminable portion of the system 100 other than illumination system 120.

Illumination system 120 may include a series of individual lighting elements or light members such as light emitting diode (LED) lights in an exemplary embodiment. The LED lights may be formed in an array and operably connected to the control module 115. It is understood that the illumination system 120 can operate and illuminate in conjunction with or completely separate from a display. The display may also include a plurality of additional lighting elements or light members, which may also take the form of LED lights in an exemplary embodiment. In certain embodiments, display may provide a visual indication of settings or goals.

LED lights of illumination system 120 may be formed in an array and may be operably connected to the control module 115. It is understood that various indicator systems can operate and illuminate in conjunction with illumination system 120 in order to provide a display. An indicator system may also include a plurality of additional lighting elements or light members, which may also take the form of LED lights in an exemplary embodiment. In certain embodiments, an indicator system may provide a visual indication of various types of information such as goals, progress towards a goal, changes in elevation or terrain, a suggested route, completion of milestone, and the like.

The control module 115 may be operably connected to additional sensors, including a time/intensity sensor 114 configured to receive a user input specifying a setting of the illumination system 120, and a mode sensor 112 configured to receive a user input specifying a mode of operation of the illumination system 120 and to power on/off the illumination system 120. The time/intensity sensor 114 and the mode sensor 112 may be positioned in particular locations on the garment so as to provide ease of access to a user to provide inputs thereon. The control module 115 may be positioned on a particular location on the garment 102 so as not to obstruct the user when the garment is worn and when performing an activity. The mode sensor 112 may include input selectors 112a and 112b corresponding to a continuous mode and a pace mode, respectively. The time/intensity sensor 114 may include input selectors, such as swipe pad 114a configured to adjust an intensity of the illumination system 120, and/or to adjust a frequency of a pulsation of the illumination system 120.

As shown in FIGS. 1A and 1B, sensor system 110 includes right side strain sensor 111a and left side strain sensor 111b, positioned on garment 102 to lie proximate to a user's right and left deltoids, respectively, when worn. Right side strain sensor 111a and left side strain sensor 111b may be located respectively over left and right deltoid muscles extending from a clavicle area, across the should and along a posterior deltoid muscle, and anchoring around the triceps muscle. Right side strain sensor 111a and left side strain sensor 111b may attach to a portion of garment 102 near a top central shoulder area in proximity to an upper end of mode sensor 112 and time/intensity sensor 114. Right side strain sensor 111a and left side strain sensor 111b may extend along should area toward a posterior end and partially down an arm area terminating near a triceps area. In some embodiments, placement of the right side strain sensor 111a and left side strain sensor 111b may resemble an epaulet. In some embodiments, data from sensor system 110 may detect that a strain at a sensor location has increased and therefore, right side strain sensor 111a may be configured to alone detect that a user's right arm has moved, e.g., indicative of an arm swing while running or jogging. With a predetermined amount of strain, a trigger may be sent to control module 115 to initiate an illumination sequence with illumination system 120 when operating in a pace mode, as will be described herein. Yet, in other embodiments, data from both the right side strain sensor 111a and the left side strain sensor 111b may be utilized in combination, either with each other or with other sensors to detect and/or measure movements. Thus, certain measurements may be determined from combining data obtained from various sensors.

Detected movements or parameters from sensor system's 104 sensor(s), may include (or be used to form) a variety of different parameters, metrics or physiological characteristics including but not limited to speed, distance, steps taken, and energy expenditure such as calories, heart rate and sweat detection. Such parameters may also be expressed in any various types of terms, including but not limited to activity points or currency earned by the user based on the activity of the user. Examples of stretchable capacitive sensors that may be utilized in accordance with various embodiments are disclosed in U.S. Pat. No. 7,958,789, and WO 2014/204323, the contents of which are incorporated herein in their entirety for any and all non-limiting purposes.

Additional sensors may be included in sensor system 110, e.g., in conjunction with the at least one stretch fabric sensor, configured to detect and/or monitor at least one athletic activity parameter of a user. Such additional sensors may include but not limited to: an accelerometer, a gyroscope, a location-determining device (e.g., GPS), a light sensor, a temperature sensor (including ambient temperature and/or body temperature), a heart rate monitor, an image-capturing sensor, a moisture sensor and/or combinations thereof.

Control module 115 may be positioned so as to not obstruct a user during an athletic activity. For example, as shown in FIG. 1B, control module 115 may be positioned in an upper or central back portion when secured to garment 102. The control module 115 may be configured to be disconnectable from the sensor system 110 and removable from the garment 102. The control module 115 may include a hermetically sealed outer shell 118 encasing electronics and other components therein. The hermetically sealed outer shell 118 may be shaped so as to contour a portion of the user in accordance with a location of the control module when affixed to the garment 102, e.g., the curve of a back of the user wearing shirt garment 102 of FIGS. 1A and 1B. In some examples, outer shell 118 may be a plastic elliptically-shaped shell, and may be designed to minimize water ingress therein. The control module 115 may include a battery and a printed circuit board assembly (not pictured) inside outer shell 118. The control module 115 may be configured to allow recharging of the battery without disassembly or removal of the battery therefrom. Battery may be removable from control module 115 by opening outer shell 118. Battery may be rechargeable with an external charger and/or may be removable from control module 115.

Figure 5:
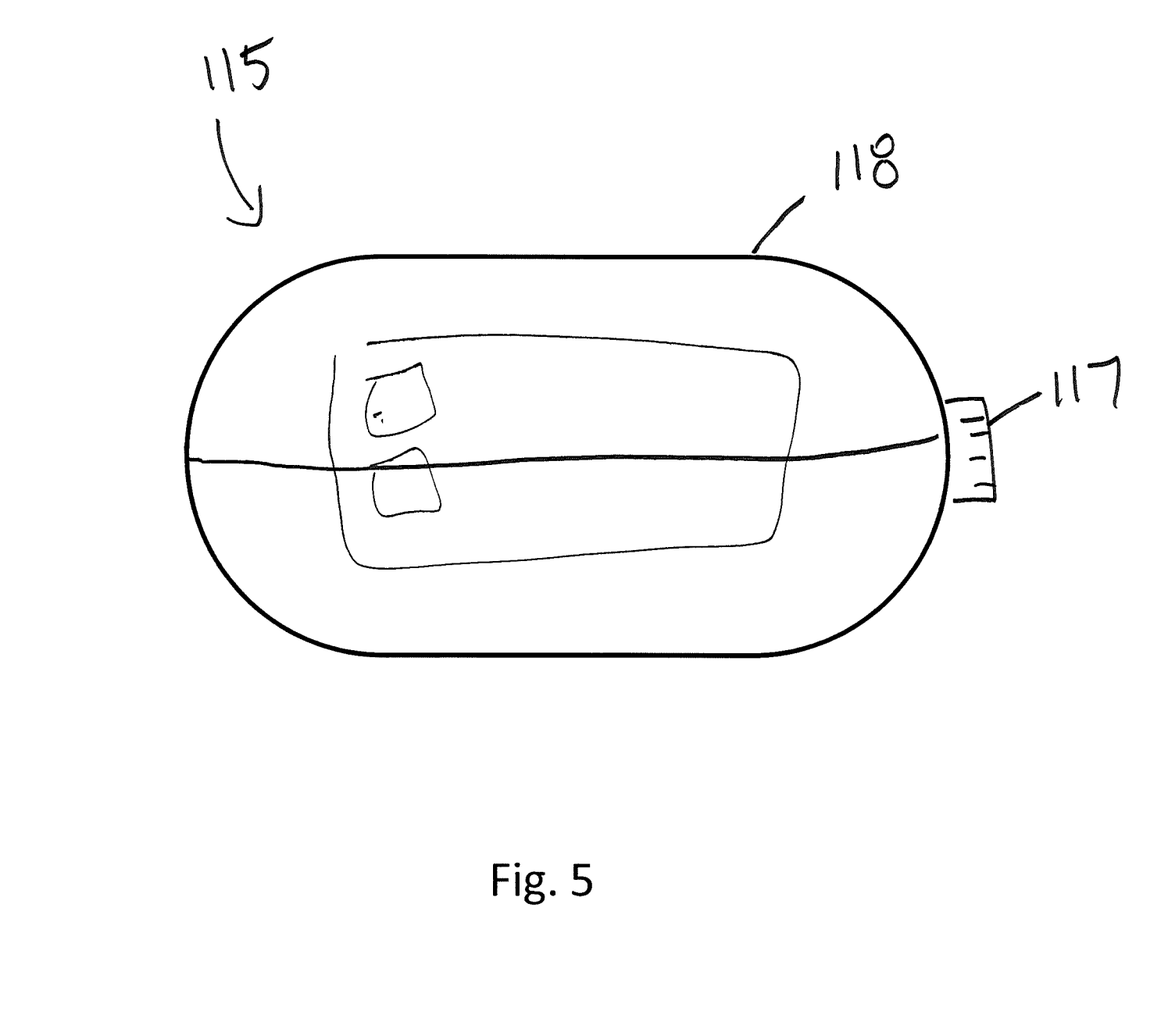
FIG. 5 illustrates a control module of the sensor-integrated apparel system of FIGS. 1A and 1B.

Outer shell 118 may be openable and closeable by various known configurations, and may be openable and closeable by use of various known tools. Control module 115 may be configured to be removable from the garment 102 and connectable to a computing device for transfer of data therebetween. All components of control module 115 may be integral with garment 102 and/or may be washable. Further, while control module 115 may be washable in part due to water resistant outer shell 118, control module 115 may still be removable from garment 102, e.g., for washing garment 102 in a washing machine. Control module 115 may be sized and designed to fit within an interior pocket of garment 102, and a body side of outer shell 118 may be contoured so as to conform to a spine curve aligned with a location of interior pocket of garment 102. Control module 115 may be connected to garment 102 via a single connector 117 on a side of control module 115, e.g., nearest to a collar of garment 102 when installed in garment 102. Control module 115 may be connectable for programming, debugging and the like via various known computer connections, such as various USB connections. For example, control module 115 may include a Mini-B USB connector exposed only when outer shell 118 is opened.

Control module 115 may be capable of data logging, e.g., in order to develop algorithms which interpret pressure profiles applied by users as they interact with the strain sensors in order to determine a pace of the user. Control module 115 may include a variety of non-transitory computer readable media, such as memory, and/or a processing device for executing software instructions, such as for example, a microprocessor device. Memory may include, but is not limited to, random access memory (RAM) and/or read only memory (ROM). Memory may include any of: electronically erasable programmable read only memory (EEPROM), flash memory or other memory technology, CD-ROM, digital versatile disks (DVD) or other optical disk storage, magnetic storage devices, or any other medium that can be used to store the desired information and that can be accessed by control module 115. Control module 115 may include memory to record and collect data from sensor system 110 at a particular sampling rate, e.g., around or greater than 20 Hz. Control module 115 may be connectable, either directly or indirectly, through a bus or alternate communication structure to one or more peripheral devices. For example, the processing unit or the system memory of control module 115 may be directly or indirectly connected to additional memory storage, such as a hard disk drive, a removable magnetic disk drive, an optical disk drive, and a flash memory card, as well as to input devices, and output devices. Data may be retrieved from control module 115 upon connecting it to another computing device. The processing unit and the system memory also may be directly or indirectly connected to one or more input devices and one or more output devices. The output devices may include, for example, a monitor display, television, printer, stereo, or speakers. The input devices may include, for example, a keyboard, touch screen, a remote control pad, a pointing device (such as a mouse, touchpad, stylus, trackball, or joystick), a scanner, a camera or a microphone. In this regard, sensor system 110 may be considered a type of input device to control module 115 that is configured to sense, detect, and/or measure athletic movement from a user. System 100 may also include touch screens or other a graphical user interface to allow a user to make various selections, e.g., for operating sensor system 110. One or more embodiments may utilize one or more wired and/or wireless technologies, alone or in combination, wherein examples of wireless technologies include Bluetooth® technologies, Bluetooth® low energy technologies, and/or ANT technologies.

Still further, control module 115, and/or any other components of sensor system 110 may be directly or indirectly connected to one or more network interfaces for communicating with a network. In one example, a network interface may include a network adapter or network interface card (NIC) configured to translate data and control signals from the control module into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface connected to control module 115 may employ any suitable connection agent for connecting to a network, including, for example, a wireless transceiver, a power line adapter, a modem, or an Ethernet connection. Network, however, may be any one or more information distribution network(s), of any type(s) or topography(s), alone or in combination(s), such as internet(s), intranet(s), cloud(s), LAN(s). Network may include any one or more of cable, fiber, satellite, telephone, cellular, wireless, etc. Network may be variously configured such as having one or more wired or wireless communication channels to connect one or more locations (e.g., schools, businesses, homes, consumer dwellings, network resources, etc.), to one or more remote servers, or to other computers.

System 100 may monitor movements of a user, including, e.g., athletic movements or other activity of user. In another embodiment, system 100 may provide visual, tactile, and/or audio information to a user during a workout or training session. For example, in one embodiment, sensor system 110 may include an activity monitor that measures, monitors, and tracks or otherwise senses the user's activity (or inactivity). Sensor system 110 may detect athletic movement or other activity (or inactivity) during user's interactions with various other components of system 100 and/or operate independently of such interaction. System 100 may communicate directly or indirectly, wired or wirelessly, with a network and/or other devices. Athletic data obtained from system 100 may be utilized in determinations conducted by a computer, such as determinations relating to exercise programs presented to a user. As used herein, athletic data means data regarding or relating to a user's activity (or inactivity). In one embodiment, system 100 may wirelessly interact with a remote website such as a site dedicated to fitness or health related subject matter, either directly or indirectly (e.g., via a mobile device, or by plugging control module 115 directly into a computing device). In this or another embodiment, system 100 may interact with a mobile device, as to an application dedicated to fitness or health related subject matter. In some embodiments, at some predetermined time(s), the user may wish to transfer data from the system 100 to another location. For example, a user may wish to upload data from a portable device with a relatively smaller memory to a larger device with a larger quantity of memory. Communication between system 100 and other devices may be done wirelessly and/or through wired mechanisms.

Figure 2:
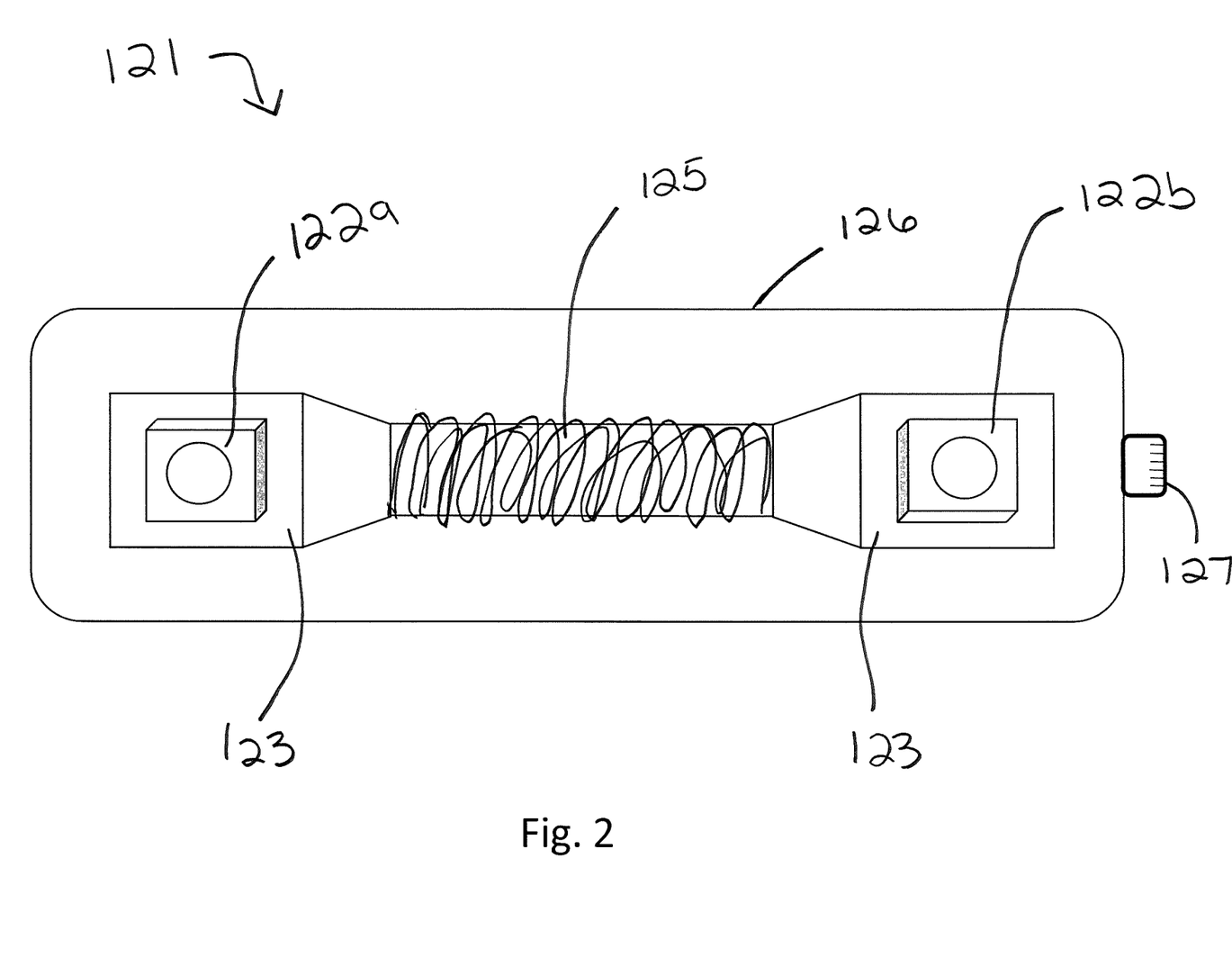
FIG. 2 illustrates an illumination system of the sensor-integrated apparel system of FIGS. 1A and 1B.

Now referring to FIG. 2, further aspects of an LED module 121 of the illumination system 120 are illustrated. Illumination may be provided by two LEDs 122a and 122b positioned on opposite ends of LED module 121 generally constructed as a strip extending along a length thereof. In some examples, a single LED may be provided in a particular location, and/or along a strip or forming any other shape along garment 102. Still in other examples, multiple additional LEDs may be provided on an LED module, and/or may be paired with other LED modules and/or positioned at various locations on garment 102. LEDs 122a and 122b are connected on a common flexible printed circuit board (PCB) 123 having a "dog bone shape," i.e., a long slender central region and a larger area on each end, where each of LEDs 122a and 122b are respectively mounted. The flexible PCB 123 and LED 122a and 122b may be similar to those known in the art, and typically found in consumer electronics. LEDs 122a and 121b may be wired in a common anode configuration with a cathode of each able to sink current for each LED 122a and 122b individually. A central armature 125 composed of a twisted wire spine may be provided around the central region of the flexible PCB 123. Central armature 125 may be similar to those used in internal bendable or posable structures of stop-motion characters, action figures, and other toys. Casing 126 may be molded over components of the illumination system 120, such as the LED modules 121a and 121b, central armature 125, and flexible PCB 123. Casing 126 may be composed of an optically clear, water impermeable and/or rubberlike material. In some examples, casing 126 may be composed of polydimethylsiloxane (PDMS), polyurethane (TPU/PU), polyester, and/or epoxy resins. Casing 126 may include a flange 127 extending in a plane of a back side of casing 126. Flange 127, may be attachable to garment 102, e.g., by sewing and/or heat bonding, thus serving as an anchor for one end of the illumination system 120 to garment 102.

In some examples, each of the LED modules 121a and 121b shown in FIG. 1A may be configured to provide illumination to a specified area proximate to a user. For example, LED modules 121a and 121b may be configured to provide illumination in a range of 5 meters, or 3 meters, in front of a wearer during use. In some examples, LED modules 121a and 121b may be configured to provide an illumination area suitable for a particular activity, e.g., in a range of 2-3 meters for a user during running. LEDs provided in LED modules 121a and 121b may be provided having a maximum instantaneous current of 50 mA and a maximum continuous current of 20 mA, and a resistance from control module 115 may be less than or within a range of 0-5 Ohms. A resistance may not be variable in some embodiments. Still other ranges of the LED modules 121a and 121b are possible without departing from the scope of the present disclosure.

In some embodiments, an illumination intensity from the LED modules 121a and 121b may be distributed from several peak positions. For example, the illumination intensity may be distributed in left and right center regions 2-3 meters ahead of the wearer and left and right 1-2 meters ahead and 1-2 meters outward from the left and right sides. In some embodiments, each LED module 121a and 121b may include a pair of LEDs. For example, LED module 121a may include an inboard right LED and an outboard right LED and LED module 121b may include an inboard left LED and an outboard left LED. The inboard right and left LEDs may be configured to direct center regions of illumination, and outboard right and left LEDs may be configured to direct right and left side illumination, respectively. In some examples, the LED modules 121a and 121b may be positioned on garment symmetrically. For example, as shown in FIG. 1A, LED modules 121a and 121b are bilaterally symmetric about a central front portion of garment 102, and may approximately line up with a first rib of a wearer and centered about a sternum of the wearer. Those skilled in the art will appreciate that other configurations are possible.

The illumination system 120 may be configured to have a targeted and/or controllable illumination area based on a selected mode or operation. For example, LED modules 121a and 121b may be shielded or directed to have no direct illumination path to the eyes of a wearer. In some example, illumination system 120 may be configured to be twisted or bent in shape, when integrated with garment 102, allowing the wearer to aim a peak of the illumination from each LED module to best suit a particular use, e.g., to narrow an illumination region while running on a narrow trail or to widen an illumination region while on a wider foot path. Further, portions of the illumination system 120 may be adjustable to tailor to a specific anatomy of a wearer. The illumination system 120 may be configured to adjust an intensity and/or a duration of illumination based on a setting from the control module 115 to which the illumination system is operably connected thereto. Connection from illumination system 120 to control module 115 may be made with wires or cables (e.g., flat formed cables) soldered or otherwise bonded to the flexible PCB 123. In some example, once the wiring or cable is connected to the flexible PCB 123, a secondary process of over-molding may be performed, e.g., to seal and provide strain relief to the wiring/cable. Over-molding may be performed with a hot-melt adhesive using a relatively low temperature and pressure process so as not to damage the wiring/cable. In some examples, the connection between the flexible PCB 123 and the wiring/cable may alternatively or additionally be sealed and strain relieved using a casting process with a two-part epoxy resin.

Figure 3:
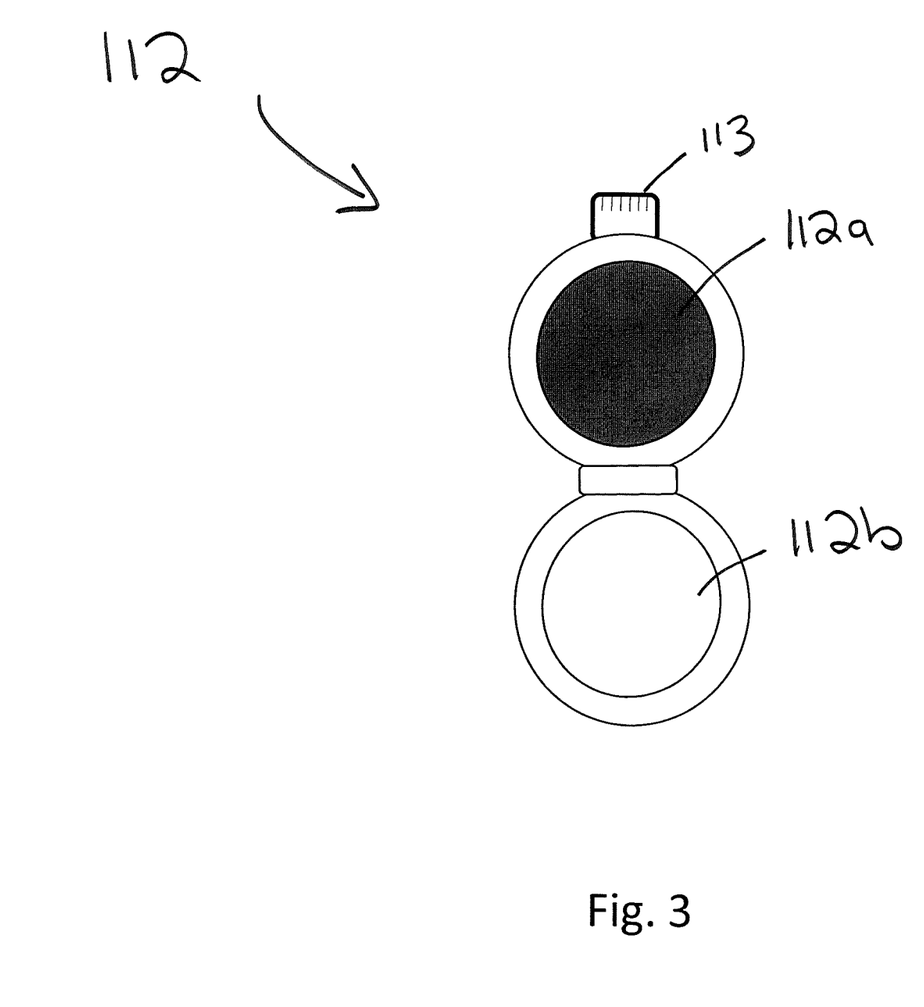
FIG. 3 illustrates a mode sensor of the sensor-integrated apparel system of FIGS. 1A and 1B.

A close-up view of mode sensor 112 is illustrated in FIG. 3. Mode sensor may be positioned on a location of garment that allows a user to access mode sensor 112 when garment 102 is worn. For example, as shown in FIG. 1A, mode sensor 112 may be positioned above a pectoral area of garment 102, when garment 102 is a shirt or jacket garment type. Mode sensor 112 may include a continuous mode input selector 112a and a pace mode input selector 112b which may be grouped onto a unitary component. Connector 113 may be provided at an end of mode sensor 112. Connector 113 may be a flat tab projecting from an end of mode sensor 112, and may be comprised of one or more conductive pads for operable connection to sensor system. When installed in garment 102, connector 113 may be positioned at an edge nearest a shoulder area of garment 102.

Figure 4:
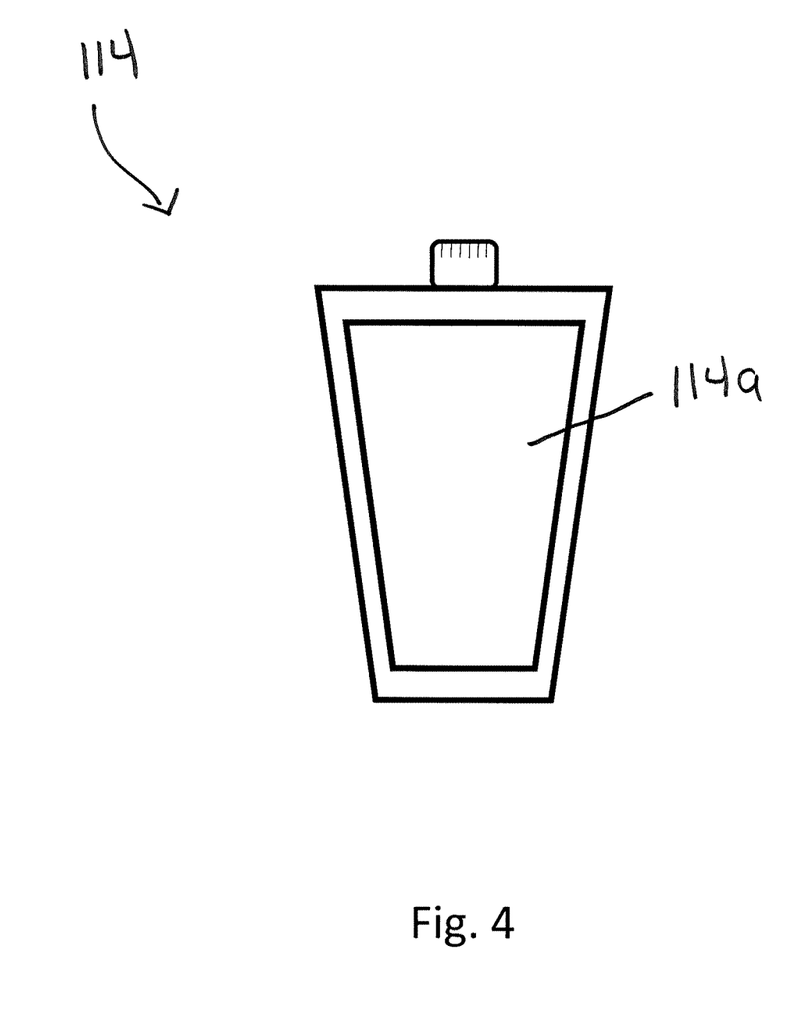
FIG. 4 illustrates a time/intensity sensor of the sensor-integrated apparel system of FIGS. 1A and 1B.

Now referring to FIG. 4, a close-up view of time/intensity sensor 114 is illustrated. Time/intensity sensor 114 may be located above a pectoral area of garment 102 on a side opposite of mode sensor 112, when garment 102 is a shirt or jacket garment type. In some examples, mode sensor 112 and time/intensity sensor 114 may be positioned symmetrically on garment 102. In some examples, mode sensor 112 and time/intensity sensor 114 may each have different shapes, colors, and/or sizes for ease of usability in distinguishing between the two. Mode sensor 112 and time/intensity sensor 114 may be of a similar size and be located bilaterally symmetric to each other. For example, mode sensor 112 may have a generally hourglass shape, with each of continuous mode input selector 112a and pace mode input selector 112b having a generally round or elliptical shape. A waist or necking may be provided between continuous mode input selector 112a and pace mode input selector 112b to increase flexibility and aid in locating mode sensor 112, thus providing the generally hourglass shape which may also allow some twistability of one end relative to another. When attached to garment 102, mode sensor 112 may be positioned such that continuous mode input selector 112a is closest to a shoulder area and pace mode input selector 112b is farther from a shoulder area of garment 102. Time/intensity sensor 114 may have a generally teardrop shape, with a larger diameter end being located nearer to a shoulder area of garment 102. Mode sensor 112 and time/intensity sensor 114 may each be shaped so as to be locatable by an edge shape or texture and/or by an overall shape.

A continuous mode input selector 112a of mode sensor 112 may be pressed to power on (and/or power off) illumination system 120 in a continuous illumination setting. In the continuous illumination setting, the time/intensity sensor 114 may be configured to receive an input to increase or decrease an illumination of illumination system 120. In the exemplary embodiment shown in FIG. 4, time/intensity sensor 114 may include a swipe pad 114a, configured to adjust an illumination intensity based on a received swiping input. Swiping upward on swipe pad 114a, e.g. from a narrower lower end toward a wider upper end, may increase the illumination intensity. Repeatedly swiping upward may increase the illumination intensity to a maximum intensity upon which further upward swiping will have no effect. Swiping downward on swipe pad 114a, e.g., from the wider upper end to the narrower lower end may decrease the illumination intensity. Repeatedly swiping downward may decrease the illumination intensity to a minimum intensity upon which further downward swiping will have no effect. In some examples, the minimum intensity may be associated with the illumination system 120 being powered off. Both illumination modules 121a and 121b may be powered on when in the continuous illumination setting. In some examples, either or both of the illumination modules 121a and 121b may be selectively powered on or off in the continuous illumination setting, e.g., in response to a user input. A change in illumination intensity based on input received on swipe pad 114a may vary a current supplied to the LED modules 121a and 121b of illumination system. The change in supplied current may be the same in both LED modules 121a and 121b. In some examples, different changes in supplied current may be applied to LED modules 121a and 121b in response to an input indicative of a differential change in illumination intensity.

A pace mode input 112b of mode sensor 112 may be pressed to power on (and/or power off) illumination system 120 in a pace-triggered illumination setting. For example, system 100 may determine a pace of a use based on a detected arm swing from right and left deltoid sensors 111a and 111b, illumination to LED modules 121a and 121b may be alternately or differentially provided based on the determined pace. In an embodiment, upon pressing pace mode input 112b, each of LED modules 121a and 121b may be configured to provide a brief flash, or other indicative signaling that illumination system 120 has been powered on. Further illumination from LED modules 121a and 121b may then occur upon a triggering signal from right and left deltoid sensors 111a and 111b associated with a detected arm swing. Right and left deltoid sensors 111a and 111b may be configured to extend and compress with each arm swing while a user in running in order to generate a trigger signal indicative of a pace of the user. While in the pace-triggered illumination setting, swipe pad 114a of the time/intensity sensor 114 may be configured to adjust an illumination duration (post triggering) based on a received swiping input. Swiping upward on swipe pad 114a, e.g., from the narrower lower end toward the wider upper end, may increase the illumination duration. Repeatedly swiping upward may increase the illumination duration to a maximum duration upon which further upward swiping will have no effect. In some examples, the maximum duration may be associated with illumination system 120 being continuously powered on. Swiping downward on swipe pad 114a, e.g., from the wider upper end to the narrower lower end may decrease the illumination duration. Repeatedly swiping downward may decrease the illumination duration to a minimum duration upon which further downward swiping will have no effect. In some examples, the minimum duration may be associated with the illumination system 120 being powered off. In some examples, if an interval between arm swing triggers is less than the illumination duration, illumination may be nearly continuous, with only a brief flash at an occurrence of a trigger. In some examples, a targeted pace illumination setting may be triggered in which the illumination system 120 triggers illumination between LED modules 121a and 121b based on a targeted pace.

In some embodiments, when in the in pace-triggered illumination setting the left LED module 121b may be configured to power both of its LEDs based on a trigger from left deltoid sensor 111b. Similarly, when in the in pace-triggered illumination setting the right LED module 121a may be configured to power both of its LEDs based on a trigger from right deltoid sensor 111a. In some embodiments, if a user stops moving while in the pace-triggered illumination setting, thus ceasing further arm swings, both LED modules 121a and 121b may be configured to cease illumination.

In some embodiments, when both continuous mode input 112a and pace mode input 112b are pressed simultaneously, e.g., for more than several seconds, illumination system 120 may be powered off. The spacing between continuous mode input 112a and pace mode input 112b may be designed so that both inputs are able to be simultaneously pressed by two fingers or by the heel of a palm of a user, thus providing ease of using system 100, particularly when a user may be fatigued following an athletic activity.

In either of the continuous illumination setting or the pace-triggered illumination setting, a ratio of current supplied to central and outboard LEDs may be fixed. Still in some examples, the ratio of current supplied to central and outboard LEDs may be adjustable. The ratio of current supplied may be adjustable in firmware and/or may be the same for both sides. Still in some embodiments, each LED may receive different ratios of current supplied, without departing from the scope of the present disclosure.

Figure 6A:
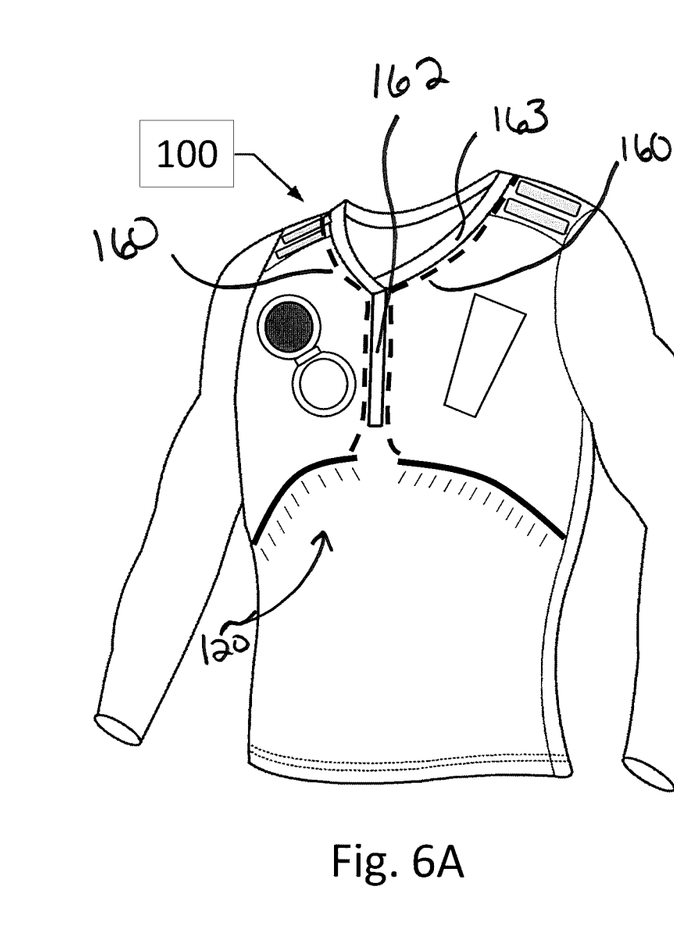
Figure 6B:
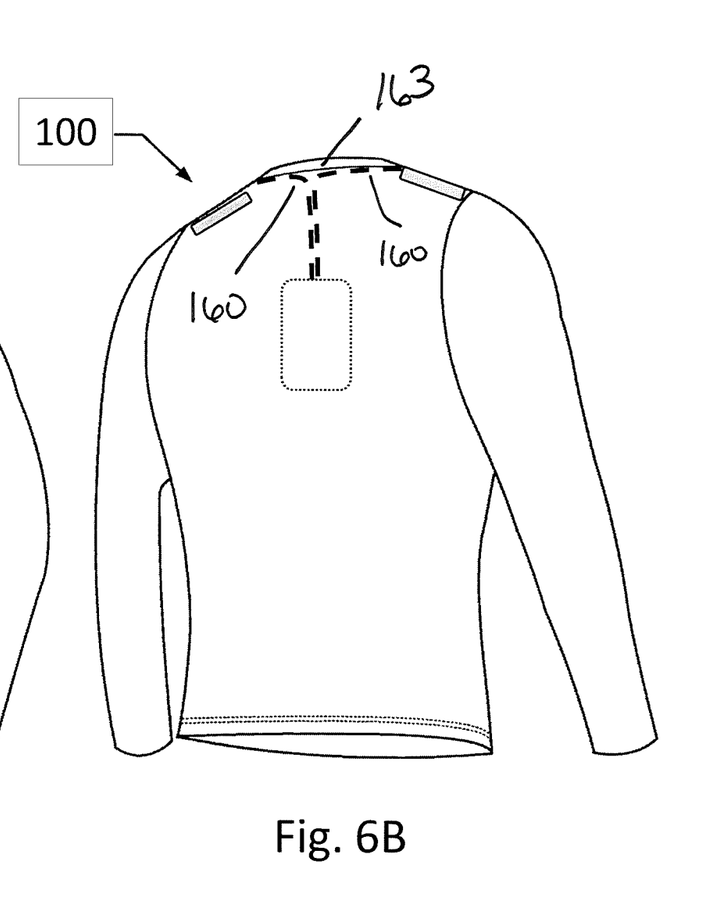

The sensor system 110, the illumination system 120, and the control module 115 may be interconnected in the garment by wiring 160 routed along seams of the garment 102, for example, as shown in FIGS. 6A and 6B. The wiring 160 may be primarily routed along seams in garment 102 so as not to impede in the perceived stretch of garment 102. Further, a sizing of the various components, e.g., including sensor system 110, control module 115 and illumination system 120, may be kept small so as to maintain stretch and flexibility of garment 102. In some embodiments, the wiring may be comprised of a flexible and thin metallized thread. For example, AmberStrand 166 metallized thread from Syscom Advanced Materials may be used. The wiring 160 may be routed to half-zipper 162 of garment 102 and then upward along each seam on either side of zipper to a seam of collar 163. The wiring 160 may then be routed around the collar 163 to the back of a neck and down to control module 115. An example embodiment of such wiring is illustrated in FIGS. 6A and 6B.

Figure 7:
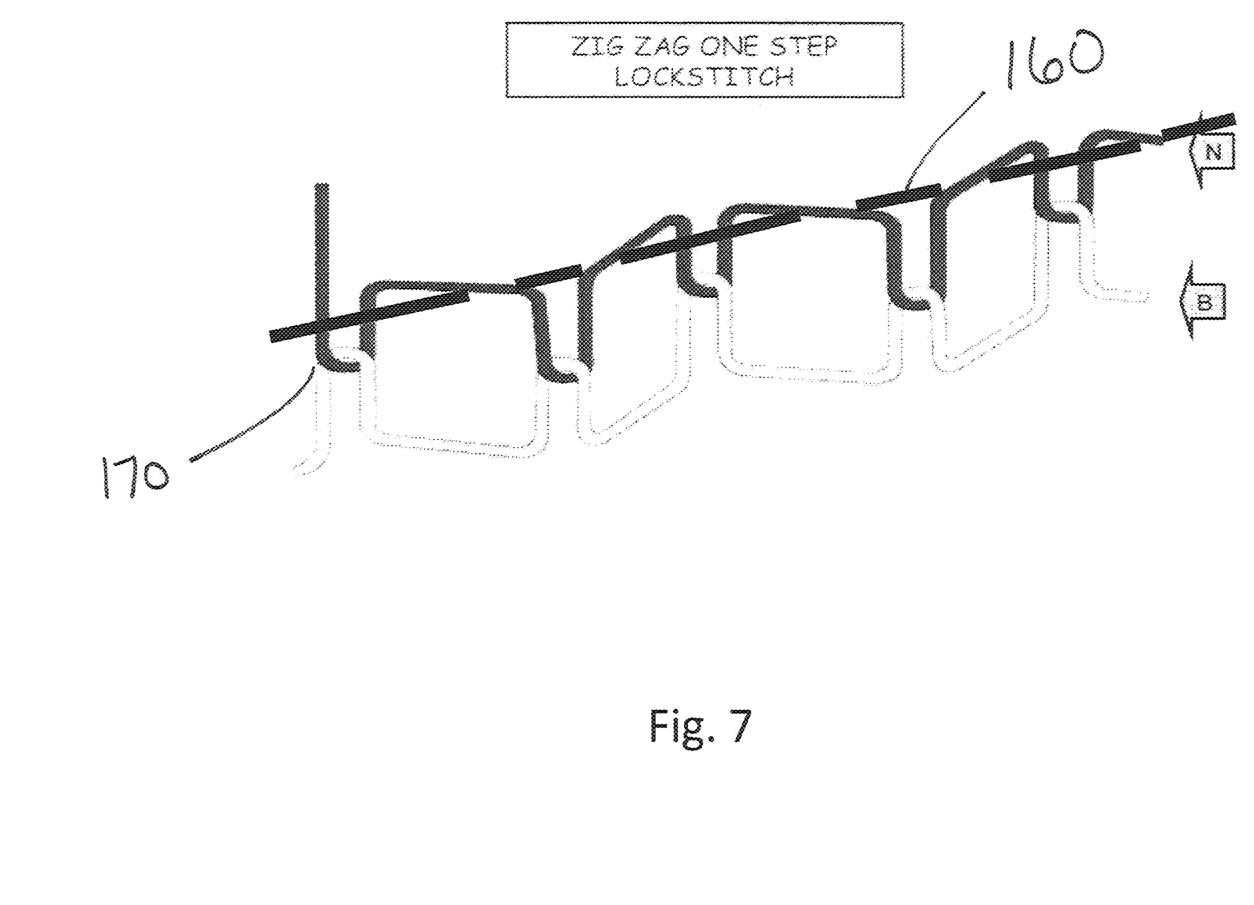
FIG. 7 illustrates a close-up view of a portion of the sensor-integrated apparel system in accordance with example embodiments.

As shown in FIG. 7, wiring 160 may be affixed to a garment using a 304 zigzag lockstitch 170 with a conductive thread applied as a cord, and with a hem line along the zipper fixtured into a flat panel. The 304 lockstitch may be sewn onto and through various flexible circuit board materials discussed herein. Wiring 160 may be aligned with and on top of conductive pads of the flexible PCB. Once in place, insulation may be removed and the wiring 160 may be brought into contact with conductive pad. For example, such a process may include positioning conductive thread/wiring over a conductive pad, stripping an insulation cover off the wiring, then stripping the insulation cover solvent off the wiring, e.g., using acetone, a microbrush with abrasion, a pressure pad, direct flow and aspiration, and the like. Next, a reinforcement of the contact points may need to be applied, e.g., using a conductive glue such as MasterSil 705/S. in some examples, a final layer of insulating material, e.g., MasterSil 709 or 710 may be provided for a rapid, air-curable and flexible coating. Such wiring affixing processes may allow the garment to be machine washable and still retain flexibility, adhesion and conductivity.

In some embodiments, interconnections between the sensor system 110, mode sensor 112 and time/intensity sensor 114 to control module 115 may be comprised of a tape including thermal plastic urethane film with conductive ink traces that is radio frequency (RF) or thermally bonded to the garment. The conductive thread may also be used to make the various connections described with respect to the wiring. However, connections with conductive thread may have a lower density than connections with tape. Combinations of flexible printed circuits, mechanical metal contacts, threading and/or wiring may interchangeably be used for interconnecting the low current, low voltage pathways interconnecting the various components described herein. Coaxial cables may also form various connections, e.g., where a gauge of cable is sufficiently small and routing is serpentine to enhance the flexibility and extendibility/compressibility of cable.

In some embodiments, a system includes an apparel piece sized and dimensioned to be worn on a user and sensor system integrated with the apparel piece. The sensor system may include at least one stretchable capacitive sensor positioned on the apparel piece so as to measure a biometric parameter of the user when the apparel piece is worn, an illumination system configured to provide illumination in a specified illumination area based on the measured biometric parameter of the user, and a control module to control one or more settings of the illumination system. The at least one stretchable capacitive sensor may include one or more sensors positioned proximate to a right deltoid when the apparel piece is worn on the user and one or more sensors positioned proximate to a left deltoid when the apparel piece is worn on the user, and the at least one stretchable capacitive sensor may be configured to sense a swing of an arm of the user to sense a pace of the user. The at least one stretchable capacitive sensor may include one or more sensors positioned proximate to at least of portion of a right leg when the apparel piece is worn on the user and one or more sensors positioned proximate to a left leg when the apparel piece is worn on the user, and the at least one stretchable capacitive sensor may be configured to sense a leg swing of the user to determine a pace of the user. The illumination system may be configured to provide a pulsed illumination with a pulsation frequency set based on the measured biometric parameter of the user. The sensor system may include a time/intensity sensor configured to receive an input from the user specifying one or more settings of the illumination system, and/or a mode sensor configured to receive an input from the user specifying one or more modes of operation of the sensor system. The mode sensor includes a continuous mode component and a pace mode component, each having a respective input. The illumination system may include a plurality of LED modules. The control module may include an intensity modifier to adjust an intensity of the illumination system and a frequency modifier to adjust a pulsation frequency of the illumination system. The control module may be configured to be disconnectable from the sensor system and removable from the apparel piece, and/or may include a hermetically sealed outer shell encasing electronic components therein. The illumination system may be configured to provide a targeted and controllable illumination area based on a selected mode of operation, and/or may be movable to adjust the specified illumination area. The at least one stretchable capacitive sensor may be configured to detect a strain based on a type of biometric movement of the user. The control module may be configured to connect to a computing device and to transfer data therebetween.

In some embodiments, a method for providing illumination from a garment as a user performs an athletic activity is provided. The method may include sensing a strain from one or more sensors located on the garment, determining a pace or predicted next movement of the user based on the sensed strain, and causing an illumination system on the garment to illuminate a portion of the user's path based on the determined pace or predicted next movement. The method may further include determining a side of a next footstrike based on the determined pace. Causing the illumination system to illuminate may then include illuminating an area of the user's path corresponding to the determine side of the next footstrike. The method may further include adjusting a duration of illumination of the user's path in response to a user-provided input. The method may further include adjusting the illumination system to provide a constant illumination in response to a user-provided input. In an embodiment, the system may prompt a user to perform one or more exercises, monitor user movement while performing the exercises, and provide the user with feedback based on their performance.

In some embodiments, a method of providing illumination from a garment as a user performs an athletic activity is provided. The method includes sensing a strain from a sensor located on the garment, determining a biometric parameter of the user based on the sensed strain, and causing an illumination system to illuminate a specified illumination area based on the determined biometric parameter. The determined biometric parameter may be a pace of the user, and the method may further include determining a side of a next footstrike based on the pace of the user, wherein the specified illumination area corresponds to the determined side of the next footstrike. The method may further include adjusting a duration of illumination by the illumination system in accordance with one or more user inputs, adjusting an intensity of illumination by the illumination system in accordance with one or more user inputs, and/or adjusting the illumination system to provide a constant illumination in accordance with one or more user inputs.

In an example, one or more sensors may be located on or proximate to the user's body at various locations, and/or sensor locations may be determined from other sensory devices. For example, sensors may be placed according to body movement regions, such as joints (e.g., ankles, elbows, shoulders, etc.) or at other locations of interest on the user's body. In this regard, sensors may be physical sensors located on/in a user's clothing, yet in other embodiments, sensor locations may be based upon identification of relationships between two moving body parts. Sensors may sense a current location of a body part and/or track movement of the body part. In one embodiment, a location may be utilized in a determination of the user's center of gravity or center of mass. For example, relationships between locations with respect to one or more other locations may be utilized to determine if a user's center of gravity has been elevated along the vertical axis (such as during a jump, or as part of a running stride). In one embodiment, various additional or alternative sensor locations may be located at about the sternum of a user and/or proximate to the naval of a user. In certain embodiments, data from sensor locations may be utilized (alone or in combination with other data) to determine the center of gravity for user and/or a change in vertical axis. In further embodiments, relationships between multiple several sensor locations may be utilized in determining orientation of the user and/or rotational forces, such as twisting of user's torso. Further, one or more locations, may be utilized to as a center of moment location or a center of moment of specific body parts or regions.

In an example, the system may make an initial postural assessment of the user as part of the initial user assessment. A computer may analyze front and side images of a user to determine a location of one or more of a user's shoulders, upper back, lower back, hips, knees, and/or ankles, depending on a type of garment.

A display or display device (not pictured) may also present one or more performance level indicators to indicate a user's performance metrics. Example metrics may include speed, quickness, power, dimensions (e.g., distance stepped or dipped, height jumped, rotation of hips or shoulders), reaction time, agility, flexibility, acceleration, heart rate, temperature (e.g., overheating), blood oxygen content, or other physical or physiological metrics. A performance level indicator may be depicted as, for example, a gauge, a speedometer, a bar-type indictor, percentage indicator, etc.

In some embodiments, the garment may be a shirt or jacket and the at least one capacitive sensor may include a pair of sensor, each positioned to correspond to right and left deltoids of the user and be configured to sense an arm swing of the user. Each deltoid sensor may be configured to sense a strain indicative of an arm swing of the user. In some embodiments, the garment may be a pair of pants or shorts, and the at least one capacitive sensor may be positioned to correspond to the right and left ankles, knees, thighs, etc. of the user and be configured to sense a pace or leg swing of the user. One skilled in the art would understand that various other combinations of garment types and sensor locations may be provided without departing from the scope of the present disclosure.

A user may possess, carry, and/or wear any number of additional other electronic devices while wearing the system which may be operably connected thereto during an athletic activity. Indeed, such devices may be used to collect, detect, and/or measure athletic data in conjunction with or separate from the system. In some embodiments, the system may be configured to transmit data to such devices. Such devices may include a portable electronic device, such as a telephone or digital music player, including an IPOD®, IPAD®, or iPhone®, brand devices available from Apple, Inc. of Cupertino, California or Zune® or Microsoft® Windows devices available from Microsoft of Redmond, Washington.

Providing an apparel system having one or more of the features described herein may provide a user with an enhanced workout experience that will encourage and motivate the user to engage in athletic activities and improve his or her fitness. Users may further adjust various settings of the apparel system to tailor a specific workout setting for a particular user in a particular workout setting.

Aspects of the embodiments have been described in terms of illustrative embodiments thereof. Numerous other embodiments, modifications and variations within the scope and spirit of the appended claims will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the disclosure.

What is claimed is:

1. A sensor-enabled apparel system comprising:
    an apparel component sized and dimensioned to be worn on a user;
    at least one stretchable capacitive sensor positioned on the apparel component so as to measure a biometric parameter of the user;
    an illumination system configured to provide a pulsed illumination with a pulsation frequency set based on the biometric parameter of the user; and
    a control module configured to control one or more settings of the illumination system in response to user input.

2. The sensor-enabled apparel system of claim 1, wherein the at least one stretchable capacitive sensor includes one or more sensors positioned proximate to a right deltoid when the apparel component is worn on the user and one or more sensors positioned proximate to a left deltoid when the apparel component is worn on the user, and wherein the at least one stretchable capacitive sensor is configured to sense a swing of an arm of the user to sense a pace of the user.

3. The sensor-enabled apparel system of claim 1, wherein the at least one stretchable capacitive sensor is configured to sense a leg swing of the user to determine a pace of the user.

4. The sensor-enabled apparel system of claim 1, wherein the illumination system is configured to provide illumination in a targeted illumination pattern based on the biometric parameter of the user.

5. The sensor-enabled apparel system of claim 1, further comprising a mode sensor configured to receive an input from the user specifying one or more modes of operation of the illumination system, wherein the mode sensor includes a continuous mode component and a pace mode component, each having a respective input.

6. The sensor-enabled apparel system of claim 1, further comprising a time/intensity sensor configured to receive an input from the user specifying one or more settings of the illumination system.

7. The sensor-enabled apparel system of claim 1, wherein the control module is configured to adjust an intensity of the illumination system.

8. The sensor-enabled apparel system of claim 1, wherein the control module is configured to be disconnectable from the illumination system and removable from the apparel component.

9. The sensor-enabled apparel system of claim 1, wherein the control module comprises a hermetically sealed outer shell encasing electronic components therein.

10. The sensor-enabled apparel system of claim 1, wherein the illumination system is configured to provide a targeted and controllable illumination area based on a selected mode of operation and the biometric parameter.

11. An apparel apparatus comprising:
an apparel component sized and dimensioned to be worn on a user; and
a sensor-based illumination system integrated with the apparel component, the sensor-based illumination system including:
at least one stretchable capacitive sensor positioned on the apparel component so as to measure a biometric parameter of the user;
an illumination system configured to provide a pulsed illumination with a pulsation frequency set based on the biometric parameter of the user; and
a control module configured to receive user input and to control one or more settings of the illumination system in accordance with received user input.

12. The apparel apparatus of claim 11, wherein the control module includes:
a time/intensity sensor configured to receive user input specifying one or more settings of the illumination system; and
a mode sensor configured to receive user input specifying one or more modes of operation of the sensor-based illumination system.

13. The apparel apparatus of claim 11, wherein the illumination system is configured to provide illumination in a targeted illumination pattern based on the biometric parameter of the user.

14. The apparel apparatus of claim 13, wherein the targeted illumination pattern of the illumination system is adjustable based on determining a predicted next movement of the user based the biometric parameter.

15. The apparel apparatus of claim 11, wherein the at least one stretchable capacitive sensor is configured to detect a strain based on a type of biometric movement of the user.

16. The apparel apparatus of claim 11, wherein the control module is configured to connect to a computing device and to transfer biometric parameter data to the computing device.

17. The apparel apparatus of claim 11, wherein the illumination system is configured to provide illumination in a targeted illumination area in accordance with a sensed path of the user, and wherein the sensed path is determined based on the biometric parameter of the user.

18. The apparel apparatus of claim 11, wherein the at least one stretchable capacitive sensor includes one or more sensors positioned proximate to a right deltoid when the apparel component is worn on the user and one or more sensors positioned proximate to a left deltoid when the apparel component is worn on the user, and wherein the at least one stretchable capacitive sensor is configured to sense a swing of an arm of the user to sense a pace of the user.

19. The apparel apparatus of claim 11, wherein the illumination system is configured to provide an illumination pattern in accordance with a sensed movement of the user based on the biometric parameter of the user.

20. A sensor system integrated with an apparel component, the sensor system including:
at least one stretchable capacitive sensor positioned on the apparel component and configured to measure a biometric parameter of a user;
an illumination system configured to provide pulsed illumination with a pulsation frequency set based on the biometric parameter of the user; and
a control module to control one or more settings of the illumination system.

* * * * *

UNITED STATES PATENT AND TRADEMARK OFFICE
CERTIFICATE OF CORRECTION

PATENT NO. : 12,213,543 B2  
APPLICATION NO. : 18/241601  
DATED : February 4, 2025  
INVENTOR(S) : Steven H. Walker

Page 1 of 1

It is certified that error appears in the above-identified patent and that said Letters Patent is hereby corrected as shown below:

On the Title Page

Column 1, Related U.S. Application Data:
Line 1, Please delete "(60)" and insert --(63)--

Signed and Sealed this
Eleventh Day of November, 2025

John A. Squires
*Director of the United States Patent and Trademark Office*